US010166256B2

(12) United States Patent
Strober et al.

(10) Patent No.: US 10,166,256 B2
(45) Date of Patent: *Jan. 1, 2019

(54) ANTI-TUMOR T CELL IMMUNITY INDUCED BY HIGH DOSE RADIATION

(71) Applicant: The Board of Trustees of the Leland Stanford Junior University, Stanford, CA (US)

(72) Inventors: Samuel Strober, Stanford, CA (US); Alexander Filatenkov, Menlo Park, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 73 days.

This patent is subject to a terminal disclaimer.

(21) Appl. No.: 15/346,333

(22) Filed: Nov. 8, 2016

(65) Prior Publication Data

US 2017/0119821 A1    May 4, 2017

Related U.S. Application Data

(63) Continuation of application No. 14/750,769, filed on Jun. 25, 2015, now Pat. No. 9,545,444, which is a continuation of application No. 13/969,376, filed on Aug. 16, 2013, now Pat. No. 9,114,157.

(60) Provisional application No. 61/695,160, filed on Aug. 30, 2012.

(51) Int. Cl.
| | |
|---|---|
| *A61K 35/17* | (2015.01) |
| *A61N 5/10* | (2006.01) |
| *A61K 41/00* | (2006.01) |
| *A61K 45/06* | (2006.01) |
| *A61K 35/12* | (2015.01) |
| *A61K 35/28* | (2015.01) |

(52) U.S. Cl.
CPC ............. *A61K 35/17* (2013.01); *A61K 35/12* (2013.01); *A61K 35/28* (2013.01); *A61K 41/00* (2013.01); *A61K 41/0023* (2013.01); *A61K 45/06* (2013.01); *A61N 5/10* (2013.01)

(58) Field of Classification Search
CPC ....... A61K 35/17; A61K 41/0023; A61N 5/10
USPC ...................................................... 424/130.1
See application file for complete search history.

(56) References Cited

U.S. PATENT DOCUMENTS

| | | | |
|---|---|---|---|
| 7,125,541 B2 | 10/2006 | Thorpe et al. | |
| 8,034,334 B2 | 10/2011 | Dudley et al. | |
| 9,114,157 B2* | 8/2015 | Strober | A61K 35/17 |
| 9,545,444 B2* | 1/2017 | Strober | A61K 35/17 |
| 2006/0165652 A1 | 7/2006 | Dudley et al. | |
| 2009/0093429 A1* | 4/2009 | Fu | A61K 38/191 |
| | | | 514/44 R |
| 2011/0064650 A1 | 3/2011 | Szalay | |
| 2011/0229504 A1* | 9/2011 | Fritsche | A61K 38/1709 |
| | | | 424/185.1 |

FOREIGN PATENT DOCUMENTS

WO        2012/054792 A2    4/2012

OTHER PUBLICATIONS

Gupta et al., "Radiotherapy Promotes Tmor-Specific Effector CDS+ T Cells via Dendritic Cell Activation", J Immunol, Jun. 8, 2012, pp. 1-9, The American Association of Immunologists, Inc., Bethesda, MD.
Melief et al., "Summit on cell therapy for cancer: The importance of the interaction of multiple disciplines to advance clinical therapy", Journal of Translational Medicine, 2011, pp. 1-5, 9:107, BioMed Central, London, United Kingdom.
Brown et al. "High-dose single-fraction radiotherapy: Exploiting a new biology?", Int J Radiat Oncol Biol Phys., Jun. 2008, pp. 324-325, 71(2), Elsevier, Amsterdam, Netherlands.
Chang et al. "Stereotactic body radiation therapy: a comprehensive review", Am J Clin Oncol., Dec. 2007, pp. 637-644, 30(6), Wolters Kluwer Health, Inc., Alphen aan den Rijn, Netherlands.
Filatenkov et al. "Ineffective vaccination against solid tumors can be enhanced by hematopoietic cell transplantation", J Immunol., Dec. 1, 2009, pp. 7196-7203, 183(11), The American Association of Immunologists, Inc., Rockville, MD.
Lee et al., "Therapeutic effects of ablative radiation on local tumor require CD8+ T cells: changing strategies for cancer treatment", Blood, Jul. 2009, pp. 589-595, 114(3), The American Society of Hematology, Washington, D.C.
Mahadevan et al., "Stereotactic body radiotherapy and gemcitabine for locally advanced pancreatic cancer", Int J Radiat Oncol Biol Phys., Nov. 1, 2010, pp. 735-742, abstract only, 78(3), Elsevier, Amsterdam, Netherlands.
Sakuishi et al. "Targeting Tim-3 and PD-1 pathways to reverse T cell exhaustion and restore anti-tumor immunity", J Exp Med., Sep. 6, 2010, pp. 2187-2194, 207(10), The Rockefeller University Press, Birmingham, AL.
Stinauer et al., "Stereotactic Body Radiation Therapy for Melanoma and Renal Cell Carcinoma: Impact of Single Fraction Equivalent Dose on Local Control", Radiation Oncol., Apr. 8, 2011, pp. 1-8, 6:34., BioMed Central Ltd., London, United Kingdom.
Tran et al., "Manufacturing of large numbers of patient-specific T cells for adoptive immunotherapy: an approach to improving product safety, composition, and production capacity", J Immunother., Sep. 2007, pp. 644-654, abstract only, 30(6), Lippincott Williams & Wilkins, Inc., Philadelphia, PA.

* cited by examiner

*Primary Examiner* — Yan Xiao
(74) *Attorney, Agent, or Firm* — Pamela J. Sherwood; Bozicevic, Field & Francis LLP

(57) ABSTRACT

Cancer treatment is provided, by irradiating an individual with a localized, high single dose or short course of doses at a primary tumor site; collecting T cells from the individual after a period of time sufficient activation of an anti-tumor response; treating the individual with an effective dose of dose of chemotherapy; and reintroducing the T cell population back to the individual.

23 Claims, 6 Drawing Sheets
(6 of 6 Drawing Sheet(s) Filed in Color)

Specification includes a Sequence Listing.

Figures 1A
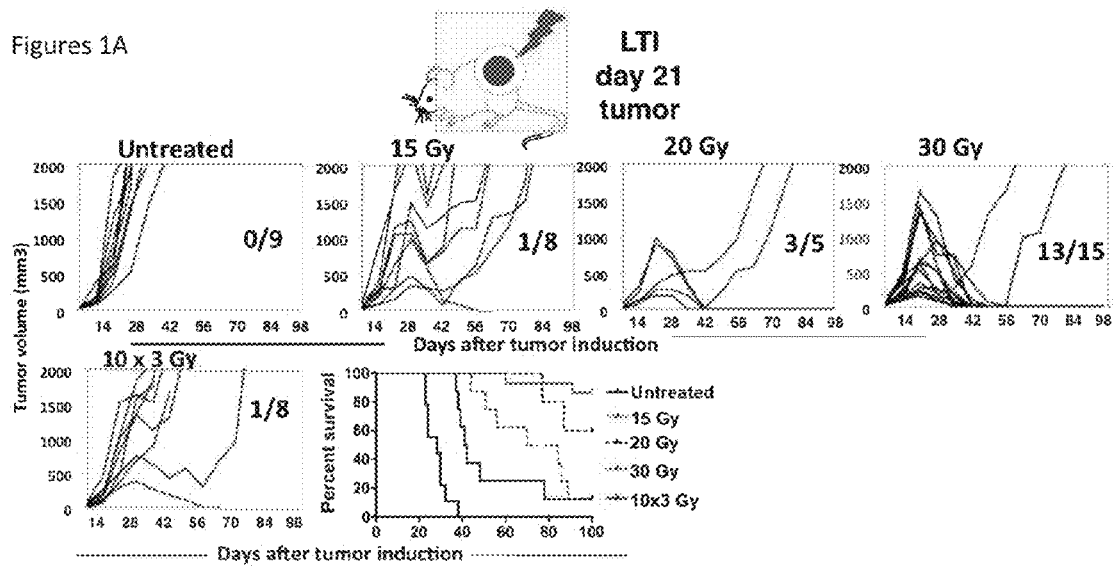
Figures 1B
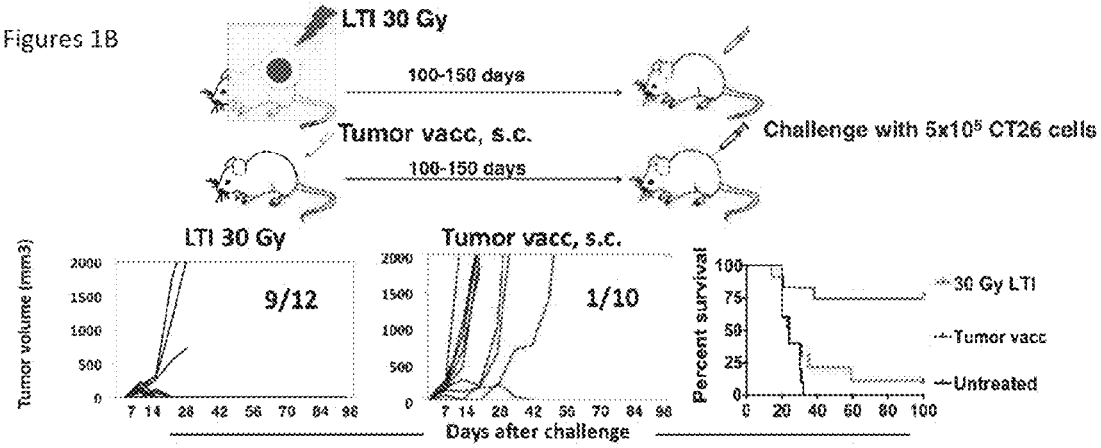
Adoptive transfer of T cells from "cured" animals into tumor-bearing syngeneic mice
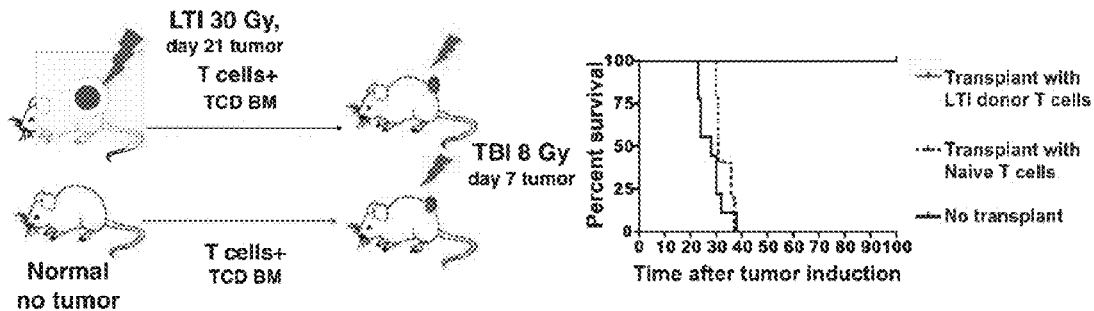
Figures 1C No LTI, day 21 tumor+
Challenge day 21

Days after second tumor cell injection

Wild type with LTI day 21 tumor

Figures 2D  RAG-2-/- with LTI day 21 tumor

Days after tumor induction

Figures 4A
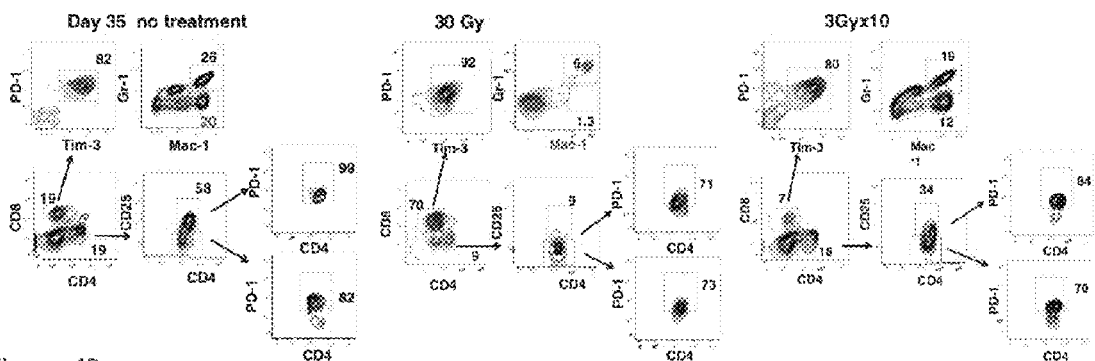
Figures 4B
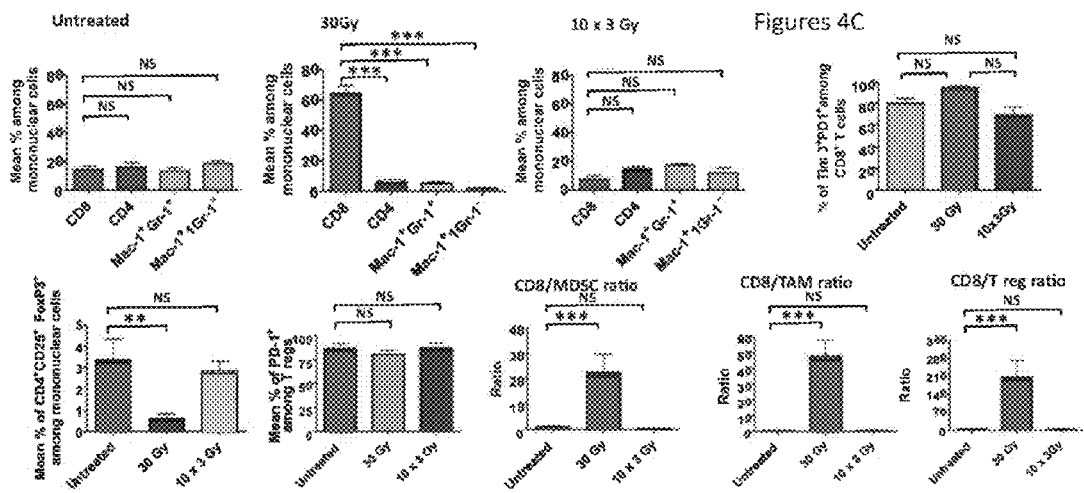
Figures 4D
Figures 4C
Figures 4E

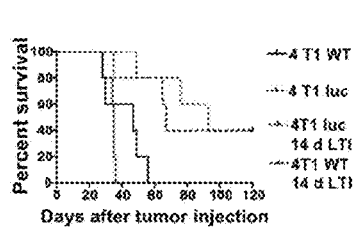
Figures 5A
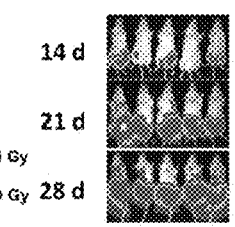
Figures 5B
Figures 5C
Lung metastasis at day 21
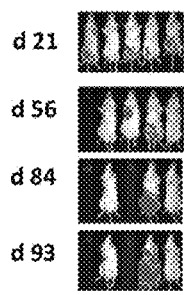
Figures 5D 60 Gy LTI at day 14
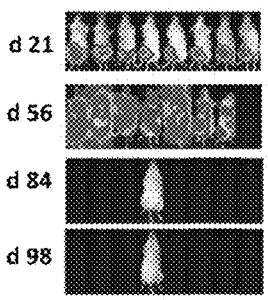
60 LTI at day 21
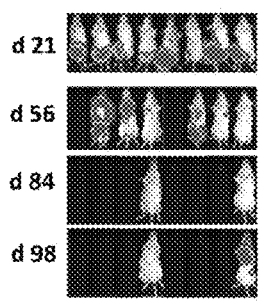
60 Gy LTI+CY at day 21
Figures 5E
Figures 5F 60 Gy LTI+CY + T cell reconstitution
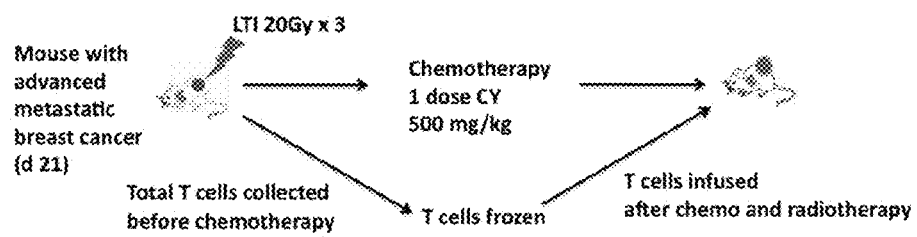
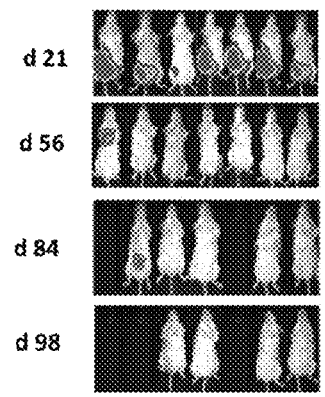
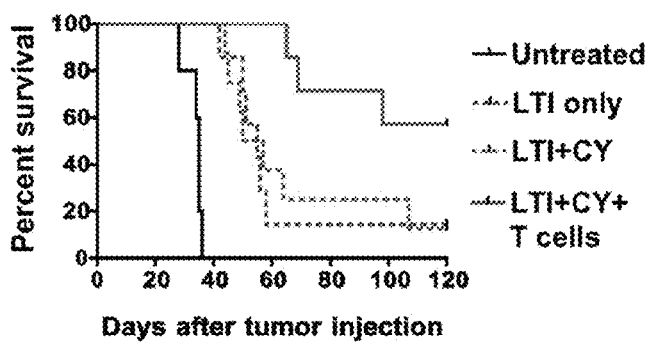

SEQUENCE LISTING

<160> NUMBER OF SEQ ID NOS: 1

<210> SEQ ID NO 1
<211> LENGTH: 20
<212> TYPE: DNA
<213> ORGANISM: Artificial Sequence
<220> FEATURE:
<223> OTHER INFORMATION: Synthetic nucleic acid sequence

<400> SEQUENCE: 1
tccatgacgt tcctgacgtt                                                                20

ANTI-TUMOR T CELL IMMUNITY INDUCED BY HIGH DOSE RADIATION

CROSS REFERENCE

This application claims benefit and is a Continuation of application Ser. No. 14/750,769, filed Jun. 25, 2015, now U.S. Pat. No. 9,545,444 issued on Jan. 17, 2017, which is a Continuation of application Ser. No. 13/969,376, filed Aug. 16, 2013, now U.S. Pat. No. 9,114,157 issued on Aug. 25, 2015, which claims benefit of U.S. Provisional Patent Application No. 61/695,160, filed Aug. 30, 2012, which patent/applications are incorporated herein by reference in their entirety.

BACKGROUND OF THE INVENTION

Cancer, also known as malignant neoplasm, is characterized by an abnormal growth of cells that display uncontrolled cell division, invasion and destruction of adjacent tissues, and sometimes metastasis to other locations in the body. There are more than 100 types of cancer, including breast cancer, skin cancer, lung cancer, colon cancer, prostate cancer, and lymphoma. Cancer is the second leading cause of death in America and it causes about 13% of all deaths. Cancer may affect people at all ages, even fetuses, but the risk for most types of cancer increases with age. Cancers can affect all animals.

Stereotactic body radiation therapy (SBRT) utilizes a three-dimensional coordinate system to achieve accurate radiation delivery. With SBRT, the radiation planning margins accounting for set-up uncertainty are minimized. This allows for greater dose-volume sparing of the surrounding normal tissues, which enables the delivery of higher and fewer fractional doses of radiation (hypofractionation). With SBRT, discrete tumors are treated with the primary goal of maximizing local control (akin to surgical resection) and minimizing toxicity. SBRT may be defined as a radiation planning and delivery technique in which a three-dimensional orientation system is used to improve targeting accuracy, typically as a hypofractionated (1-5 fractions) regimen.

Despite these new agents and improved combinations, the current treatment is still not effective for many types of cancers or cancers at different stages. Improved regimens and treatments are greatly needed for cancer therapy.

SUMMARY OF THE INVENTION

Methods are provided for the treatment of cancer in an individual. The methods of the invention provide for an initial localized, high single dose or short courses of high doses of radiation at a tumor site of the individual; collection of T cells from the individual after a period of time sufficient activation of an anti-tumor response, for example from about 2 weeks to about 5 weeks; a dose of chemotherapy, which may be a conventional or a myeloablative dose; followed by reinfusion of the T cell population back to the individual. The methods of the invention can provide for a durable complete remission of a primary tumor. The methods of the invention can also prevent the growth of tumor metastases at a site other than the site of radiation.

In some embodiments the cancer is a solid tumor, which may be in advanced state, up to and including a metastatic state. Tumors of interest include those with at least one tumor at a body location that are amenable to focused high dose radiation, including without limitation cancers of the liver, lung, brain, pancreas, melanoma, breast, and the like.

T cells are typically collected from blood samples, e.g. by apheresis. The cells are optionally subjected to a selection process following collection, e.g. to select for T cells, to purge tumor cells, etc. The cells may be stored or cultured after collection, e.g. by freezing etc., as known in the art.

In the treatment of individuals Where the chemotherapy is a myoablative chemotherapy, the collection and reinfusion of cells may further comprise collection and reinfusion of hematopoietic stem cells in addition to T cells, for example utilizing mobilized peripheral blood as a source of cells. Alternatively the activated T cells are combined with hematopoietic stem cells, which may be autologous, or may be from an allogeneic donor.

BRIEF DESCRIPTION OF THE DRAWINGS

The invention is best understood from the following detailed description when read in conjunction with the accompanying drawings. The patent or application file contains at least one drawing executed in color. Copies of this patent or patent application publication with color drawing(s) will be provided by the Office upon request and payment of the necessary fee. It is emphasized that, according to common practice, the various features of the drawings are not to-scale. On the contrary, the dimensions of the various features are arbitrarily expanded or reduced for clarity. Included in the drawings are the following figures.

FIGS. 1A-1C. Treatment of advanced CT26 tumors by high dose radiation leads to complete remission, and development of systemic long-term immunity that can be adoptively transferred by T cells. FIG. 1A, Experimental scheme. Advanced CT26 colon tumors were established for 21 days subcutaneously and mice received a single dose of local tumor irradiation (LTI). Tumor growth curves after single doses of irradiation 15, 20 and 30 Gy, or without radiation, or with 10 doses of 3 Gy daily are shown as well as fraction of cured mice and survival. There were significant differences in survival in groups with untreated tumors vs tumors treated with 15 Gy ($p<0.05$) or 10×3 Gy or in groups treated with 30 Gy vs 15 Gy ($p<0.05$) or 30 Gy vs 10×3 Gy ($p<0.05$) by Mantel-Cox test. FIG. 1B, Experimental scheme. Mice with 21 day tumors were selected for those with complete remissions after 30 Gy of LTI (n=12). As controls, a group of normal mice was vaccinated subcutaneously (s.c.) with $1\times10^6$ irradiated tumor cells (50 Gy in vitro) and 30 μg CpG (n=10). Vaccinated or irradiated mice were challenged with $5\times10^6$ of CT26 cells subcutaneously 100-150 days after treatment. Tumor growth curves, fraction of protected mice and survival are shown. There were significant differences in survival of vaccinated or untreated vs irradiated mice ($p<0.05$). FIG. 1C, Experimental scheme. T cells ($6\times10^6$) and T cell depleted (TCD) bone marrow cells ($1\times10^7$) were harvested from mice that were cured by 30 Gy for at least 100 days, and transferred into syngeneic tumor-bearing mice (7 day tumors) conditioned with 8 Gy of total body irradiation (TBI). T cells and TCD bone marrow transfer from untreated mice served as controls. Survival for 100 days is shown. There was a significant difference in survival between groups without the transplant procedure vs with transplants from LTI donors ($p<0.05$), but not with transplants from naïve mice ($p>0.1$).

FIGS. 2A-2E. Kinetics of LTI induced resistance to tumor challenge, abrogation of remissions in T cell deficient hosts, and restoration of remissions after T cell injection. FIG. 2A, Primary CT26 tumors were established at day 0. Tumor-bearing animals were challenged with $5\times10^6$ CT26 cells on the opposite flank at day 21. Growth curves of the second tumor and fraction of mice with progressive second tumor growth are shown (n=5). FIG. 2B, 30 Gy LTI to primary tumor was given at day 21, and mice were challenged with 5×10$^6$ of CT26 cells on the opposite flank at days 21 or 51 after primary tumor implantation. There was a significant difference in the fraction without tumor growth in groups with LTI challenged at day 21 vs 51 (p<0.05 by Chi Square test). FIG. 2C, Wild-type animals with 21 day CT26 tumors received 30 Gy LTI and anti-CD8 or CD4 depleting antibodies or ATS. There were significant differences in survival between groups given LTI alone vs LTI+CD8 depletion (p<0.001) or vs LTI+CD4 depletion (p<0.01), or vs ATS (p<0.001) or no treatment (p<0.001). FIG. 2D, Tumor-bearing BALB/C RAG2$^{-/-}$ mice received 30 Gy LTI alone on day 21, or LTI+6×10$^6$ BALB/c splenic T cells on day 23 with or without CY injection (500 mg/kg i.p. immediately after LTI). Survival of tumor bearing animals is shown. There were significant differences in survival between groups given LTI alone vs LTI+CY+ T cells (p<0.001) or groups given LTI+ T cells vs LTI+ T cells+CY (p<0.05) or LTI+CY without T cells vs LTI+CY+ T cells (p<0.01). FIG. 2E, Bioluminescence imaging (BLI) of CT26 luc$^+$ bearing RAG2$^{-/-}$ mice given 30 Gy LTI on day 21+CY (500 mg/kg i.p. just after LTI), or LTI+CY+6×10$^6$ BALB/c splenic T cells (d 23). Empty boxes indicate death of mice.

FIG. 3A, Tumor-infiltrating cells and splenocytes were analyzed at day 21 after CT26 tumor implantation for expression of CD25, PD-1 and Tim-3 on CD4$^+$ and CD8$^+$ T cells, and for MDSCs (Mac-1$^+$ Gr1$^-$) and TAMs (Mac-1$^+$ Gr1$^-$). Percentages of each subset in boxes on representative two color analysis panels are shown, and arrows identify gated subsets. Staining for Mac-1, Gr-1, CD4 and CD8 used monuclear gate. FIG. 3B, Cell subsets (CD8$^+$, CD4$^+$, Mac-1$^+$Gr-1$^+$ and Mac-1$^+$Gr-1$^-$) are shown as a mean percentage+/−SE among mononuclear cells in tumor and spleens at day 21 after tumor implantation, and mean percentage of "exhausted" Tim-3$^+$ PD-1$^+$ cells shown among total CD8$^+$ T cells. FIG. 3C, Mean percentage of T reg cells and expression of PD-1$^+$ on Treg cells in tumors and spleens are shown. N=5. *−p<0.05, −p<0.01,*−P<0.001, NS p>0.05.

FIGS. 4A-4E. Single dose of 30 Gy LTI changes the balance of tumor infiltrating cells to favor CD8$^+$ T cells, and to reduce MDSC, TAMs and T regs. FIG. 4A, Mice with advanced 21 day tumors received a single dose of LTI (30 Gy) or fractionated daily doses LTI (3 Gy×10). Single cell suspensions were prepared from tumors 14 days after LTI completion. Control tumor-bearing mice received no LTI and cells were analyzed at day 35. Representative stainings of CD4$^+$ and CD8$^+$ T cells, MDSCs and TAMs are shown as well as the expression of PD-1 and Tim-3. FIG. 4B, Mean percentages+/−SE of tumor-infiltrating cells in mononuclear cell gate are shown. FIG. 4C, Mean percentage of Tim-3$^+$ PD-1$^+$ cells among tumor-infiltrating CD8+ T cells. FIG. 4D, Mean percentage of CD4$^+$CD25$^+$Foxp3$^+$ cells among mononuclear cells and mean percentage of PD-1$^+$ cells among CD4$^+$CD25$^+$Foxp3$^+$ cells. FIG. 4E, CD8/MDSC, CD8/TAM and CD8/Treg ratio in tumors in untreated animals, and animals that received LTI (30 Gy) or fractionated LTI (3 Gy×10). Mean ratios+/−SE are shown. *−p<0.05, −p<0.01,*−P<0.001, NS p>0.05.

FIG. 5A-5F. T cell therapy facilitates complete remissions of 4T1 breast tumor metastases when used in combination with radiotherapy and chemotherapy. FIG. 5A, Survival of mice given subcutaneous injections of 1×10$^4$ of 4T1 wild-type tumor cells and 4T1 luc$^+$ tumor cells compared to survival of 4T1 WT or 4T1 luc$^+$ bearing mice given 60 Gy (3 daily doses of 20 Gy each) LTI on days 14,15,16. FIG. 5B, Bioluminescence imaging (BLI) of mice at serial time points after injection of 4T1 luc$^+$ tumor cells. Note signals above diaphragm at days 21 and 28. FIG. 5C, Representative tissue section (H&E, × magnification) of lung showing tumor cell cluster in untreated mouse. FIG. 5D, BLI of mice given 4T1 luc$^+$ tumor cells after 60 Gy (3 daily doses of 20 Gy each) LTI on days 14,15,16 as well as 21, 22 and 23. Blank areas indicate death of mice. FIG. 5E, BLI of mice given 4T1 luc$^+$ cells, 60 Gy (3 daily doses of 20 Gy each) LTI, and i.p injection of CY (500 mg/kg) on day 23. FIG. 5F, mice were given 4T1 luc$^+$ cells and LTI and CY as in E, and Thy 1.2+ T cells were harvested just before CY injection on day 23. T cells were cryopreserved, then thawed and injected (5×10$^6$) i.v. 48 hr after injection of CY. BLI at serial time points is shown, as well as survival of untreated and experimental groups. There were significant differences in survival of groups given LTI alone or LTI+CY vs LTI+CY+ T cells (p<0.05), but not in groups given LTI+CY vs LTI alone (p>0.05).

DEFINITIONS

Figure 2A:
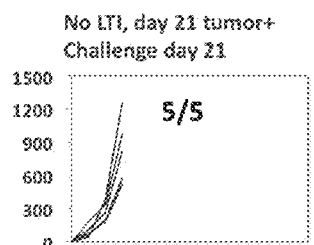

To facilitate understanding of the invention, the following definitions are provided. It is to be understood that, in general, terms not otherwise defined are to be given their meaning or meanings as generally accepted in the art.

All publications, patents, and patent applications mentioned in this specification are herein incorporated by reference to the same extent as if each individual publication, patent, or patent application was specifically and individually indicated to be incorporated by reference.

Other embodiments of the invention will be apparent to those skilled in the art from a consideration of the specification or practice of the invention disclosed herein. It is intended that the specification and Examples be considered as exemplary only, with the true scope of the invention being indicated by the appended claims.

Subject, for the purposes of the present invention, refers to an individual that has been diagnosed with cancer and is in need of treatment. Usually the subject is a mammal, where mammal refers to any animal classified as a mammal, including humans, domestic and farm animals, and zoo, sports, or pet animals, such as dogs, horses, cats, cows, etc. Preferably, the mammal is human.

Prognostic and predictive information. As used herein the terms prognostic and predictive information are used interchangeably to refer to any information that may be used to foretell any aspect of the course of a disease or condition either in the absence or presence of treatment. Such information may include, but is not limited to, the average life expectancy of a patient, the likelihood that a patient will survive for a given amount of time (e.g., 6 months, 1 year, 5 years, etc.), the likelihood that a patient will be cured of a disease, the likelihood that a patient's disease will respond to a particular therapy (wherein response may be defined in any of a variety of ways). Prognostic and predictive information are included within the broad category of diagnostic information.

Response. As used herein a response to treatment may refer to any beneficial alteration in a subject's condition that occurs as a result of treatment. Such alteration may include stabilization of the condition, e.g. prevention of deterioration that would have taken place in the absence of the treatment, amelioration of symptoms of the condition, improvement in the prospects for cure of the condition, etc. One may refer to a subject's response or to a tumors response. In general these concepts are used interchangeably herein.

Tumor or subject response may be measured according to a wide variety of criteria, including clinical criteria and objective criteria. Techniques for assessing response include, but are not limited to, clinical examination, chest X-ray, CT scan, MRI, ultrasound, endoscopy, laparoscopy, presence or level of tumor markers in a sample obtained from a subject, cytology, histology. Many of these techniques attempt to determine the size of a tumor or otherwise determine the total tumor burden. The exact response criteria can be selected in any appropriate manner, provided that when comparing groups of tumors and/or patients, the groups to be compared are assessed based on the same or comparable criteria for determining response rate. One of ordinary skill in the art will be able to select appropriate criteria.

Clinical efficacy can be measured by any method known in the art. In some embodiments, clinical efficacy of the subject treatment method is determined by measuring the clinical benefit rate (CBR). The clinical benefit rate is measured by determining the sum of the percentage of patients who are in complete remission (CR), the number of patients who are in partial remission (PR) and the number of patients having stable disease (SD) at a time point at least 6 months out from the end of therapy. The shorthand for this formula is CBR=CR+PR+SD months. In some embodiments, CBR for the subject treatment method is at least about 50%. In some embodiments, CBR for the subject treatment method is at least about 55%, 60%, 65%, 70%, 75%, 80%, 85%, 90%, 95% or more.

Sample. As used herein, a sample obtained from a subject may include, but is not limited to, any or all of the following: a cell or cells, a portion of tissue, blood, serum, ascites, urine, saliva, and other body fluids, secretions, or excretions. The term "sample" also includes any material derived by processing such a sample. Derived samples may include nucleotide molecules or polypeptides extracted from the sample or obtained by subjecting the sample to techniques such as amplification or reverse transcription of mRNA, etc.

Tumor sample. The term "tumor sample" as used herein is taken broadly to include cell or tissue samples removed from a tumor, cells (or their progeny) derived from a tumor that may be located elsewhere in the body (e.g., cells in the bloodstream or at a site of metastasis), or any material derived by processing such a sample. Derived tumor samples may include nucleic acids or proteins extracted from the sample or obtained by subjecting the sample to techniques such as amplification or reverse transcription of mRNA, etc.

High dose radiation. As used herein, high dose radiation refers to the localized delivery of radiation doses where a high level of radiation is delivered in a small number of doses over a short period of time. Generally the radiation is delivered by stereotactic body radiation therapy (SBRT), as the level of radiation is sufficient to damage normal tissues.

The total dose of radiation to the targeted site is usually at least about 20 Gy, at least 25 Gy, at least 30 Gy, and not more than 60 Gy usually not more than 40 Gy, delivered over a period of less than one week, for example in a single dose, in 3 fractionated doses over a period of from 1 to 3 days, in 2 fractionated doses over a period of from 1 to 5 days, etc. In a fractionated dose each dose may be the same or different, but in sum will not exceed to the total dose indicated above. In some tissues it may be desirable to have a fractionate so that a single dose is less than 20 Gy, less than 15 Gy, less than 10 Gy.

SBRT requires a means to detect and process a three-dimensional array. Various three-dimensional coordinate systems can be used, including internal fiducials, external markers and/or image guidance. Image guided radiation therapy (IGRT), with daily CT imaging, ultrasound and/or orthogonal x-rays can assist in targeting accuracy. Several other tools can be used to improve immobilization including stereotactic body frames, abdominal compression devices and vacuum bags. Respiratory gating, which allows for the radiation beam to be turned off when respiratory movements place the target outside of the pre-determined positioning parameters, and for radiation to resume when the target falls back within the accepted alignment, can help improve targeting. Some SBRT systems (such as Cyberknife®) track three-dimensional coordinates in real time, while the head of the accelerator realigns itself in real time to accommodate fluctuations in the target position.

The planning and delivery of SBRT generally uses multiple non-coplanar and/or arcing fields, directed at the radiation target. As result, the dose gradient is steeper than with conventional radiation, though the low dose region encompasses a larger volume and is irregularly shaped. The dose with SBRT is generally prescribed to the isocenter and/or isodose line encompassing the target, resulting in an inhomogeneous dose delivery in which the isocenter receives a greater dose than the periphery of the target. To reduce dose to surrounding tissues, a lower isocenter dose is selected and/or the dose is prescribed to a higher isodose line. With hypofractionated SBRT, versus conventional radiation, the absolute prescribed radiation dose is less (due to the use of larger, more biologically effective dose fractions).

SBRT is well suited for the sparing of tumors involving or abutting parallel functioning tissues, for example kidneys, lung parenchyma and liver parenchyma, in which functional subunits are contiguous, discrete entities. SBRT reduces the organ volume, and thus the absolute number of parallel functioning subunits destroyed by radiation. Because of an organ reserve, with redundancy of function, the undamaged functional subunits can maintain the organ function and/or regenerate new functional subunits (as occurs in liver). Serial functioning tissues such as spinal cord, esophagus, bronchi, hepatic ducts and bowel, which are linear or branching organs, in which functional subunits are undefined, may also benefit from reduced high-dose volume exposure.

Bone marrow transplantation has become well established in the treatment of malignant disorders. High-dose chemotherapy with hematopoietic stem cell support is widely used for most hematological malignancies, as well as for some solid tumors. In light of recent developments in blood progenitor cell harvest, in particular, the availability of large numbers of blood stem cells, mobilized by granulocyte colony-stimulating factor and collected by leukapheresis, it is possible to overcome histocompatibility barriers in HLA-mismatched patients. Other recent developments including but not limited to new methods for blood progenitor cells mobilization and ex vivo expansion of progenitor cells and immune cells, the use of umbilical cord blood as an alternative source of stem cells, and other molecular techniques, support an effective treatment of cancer via autologous or allogeneic transplantation of hematopoietic and immune cells.

Autologous HSCT requires the extraction (apheresis) of hematopoietic stem cells (HSC) from the patient and storage of the harvested cells in a freezer. The patient is typically treated with high-dose chemotherapy with or without radiotherapy with the intention of eradicating the patient's malignant cell population at the cost of partial or complete bone marrow ablation (destruction of patient's bone marrow function to grow new blood cells). The patient's own stored stem cells are then returned to his/her body, where they replace destroyed tissue and resume the patient's normal blood cell production. Autologous transplants have the advantage of lower risk of infection during the immune-compromised portion of the treatment since the recovery of immune function is rapid. Also, the incidence of patients experiencing rejection (graft-versus-host disease) is very rare due to the donor and recipient being the same individual. These advantages have established autologous HSCT as one of the standard second-line treatments for such diseases as lymphoma (Canellos, George (1997) The Oncologist 2 (3): 181-183).

DETAILED DESCRIPTION OF THE EMBODIMENTS

Methods are provided for the treatment of cancer in an individual. The methods of the invention provide for an initial localized, high single dose or short course of doses of radiation at a primary tumor site of the individual; collection of T cells from the individual after a period of time sufficient activation of an anti-tumor response, for example from about 2 weeks to about 6 weeks; a dose of chemotherapy, which may be a conventional or a myeloablative dose; followed by reinfusion of the T cell population back to the individual. The methods of the invention are performed in the absence of vaccination with tumor cells.

The methods of the invention can provide for a durable complete remission of a primary tumor. The methods of the invention can also prevent the growth of tumor metastases at a site other than the site of radiation.

Cancer immunotherapy is the use of the immune system to reject cancer. The methods stimulate a patient's immune system to attack malignant tumor cells that are responsible for disease. This can be through manipulating the patient's own immune system to recognize tumor cells as targets to be destroyed. Many kinds of tumor cells display unusual antigens that are either inappropriate for the cell type and/or its environment, or are only normally present during the organisms' development (e.g. fetal antigens). Examples of such antigens include but are not limited to the glycosphingolipid GD2, a disialoganglioside that is normally only expressed at a significant level on the outer surface membranes of neuronal cells, where its exposure to the immune system is limited by the blood-brain barrier. GD2 is expressed on the surfaces of a wide range of tumor cells including neuroblastoma, medulloblastomas, astrocytomas, melanomas, small-cell lung cancer, osteosarcomas and other soft tissue sarcomas. Other kinds of tumor cells display cell surface receptors that are rare or absent on the surfaces of healthy cells, and which are responsible for activating cellular signal transduction pathways that cause the unregulated growth and division of the tumor cell. Examples include ErbB2, a constitutively active cell surface receptor that is produced at abnormally high levels on the surface of breast cancer tumor cells.

However, cancer cells utilize multiple immunosuppressive mechanisms to evade T-cell responses, either to avoid immune recognition or to disable effector T-cells. These include alterations of components of the antigen presentation machinery, defects in proximal TCR signaling, secretion of immunosuppressive and proapoptotic factors, activation of negative regulatory pathways and specific recruitment of regulatory cell populations. These mechanisms limit the ability of the immune system to restrain the tumor and the effectiveness of immunotherapy strategies to successfully eradicate malignant cells.

Tumor antigen processing and presentation by APCs is the dominant mechanism underlying the development of tumor antigen-specific $CD4^+$ T-cell tolerance. Dendritic cells (DCs) in particular, play a critical role in the decision leading to T-cell tolerance versus T-cell priming in vivo. Such a decision is greatly influenced by the environmental context in which the antigen is encountered by DCs. While antigen encounter by DCs in an inflammatory context trigger their maturation to a phenotype capable of generating strong immune responses, antigen capture by DCs in a non-inflammatory environment fails to elicit productive T-cell responses, leading instead to the development of T-cell tolerance. As tumor progresses, its microenvironment not only fails to provide inflammatory signals needed for efficient DC activation, but generates additional immunosuppressive mechanisms such as IL-10 and vascular endothelial growth factor (VEGF) that further impact negatively upon DC's maturation and/or function.

Without being bound by theory, it is believed that a high dose of radiation localized to the site of a tumor can alter the immunosuppressive environment of the tumor through killing of undesirable regulatory cells, altering the antigen-presenting cells present at the site of the tumor, and the like. In immunocompetent animals, high-dose tumor radiation changes the balance between CD8+ effector cells and T regulatory cells, myeloid derived suppressor cells (MDSCs), tumor-associated macrophages (TAMs) in favor of CD8+ effector T cells, and promote immunologically mediated tumor rejection. However, the increased responsiveness of host T cells to the tumor is ineffective when followed by chemotherapy, because the nascent desirable response is ablated by chemotherapy. The methods of the invention protect these activated anti-tumor T cells by collecting them prior to chemotherapy and reinfusing to the patient after the completion of chemotherapy. In this way a durable immune response against the tumor is obtained. No specific tumor antigen immunization is required for tumor eradication. The methods of the invention significantly improve survival after high dose radiotherapy of advanced solid tumors by harvesting T cells after radiotherapy, and reinfusing after chemotherapy.

Methods of Treatment

In the methods of the invention, an individual diagnosed with cancer is treated. The types of cancer that can be treated using the subject methods of the present invention include but are not limited to adrenal cortical cancer, anal cancer, aplastic anemia, bile duct cancer, bladder cancer, bone cancer, bone metastasis, brain cancers, central nervous system (CNS) cancers, peripheral nervous system (PNS) cancers, breast cancer, cervical cancer, childhood Non-Hodgkin's lymphoma, colon and rectum cancer, endometrial cancer, esophagus cancer, Ewing's family of tumors (e.g. Ewing's sarcoma), eye cancer, gallbladder cancer, gastrointestinal carcinoid tumors, gastrointestinal stromal tumors, gestational trophoblastic disease, Hodgkin's lymphoma, Kaposi's sarcoma, kidney cancer, laryngeal and hypopharyngeal cancer, liver cancer, lung cancer, lung carcinoid tumors, Non-Hodgkin's lymphoma, male breast cancer, malignant mesothelioma, multiple myeloma, myelodysplastic syndrome, myeloproliferative disorders, nasal cavity and paranasal cancer, nasopharyngeal cancer, neuroblastoma, oral cavity and oropharyngeal cancer, osteosarcoma, ovarian cancer, pancreatic cancer, penile cancer, pituitary tumor, prostate cancer, retinoblastoma, rhabdomyosarcoma, salivary gland cancer, sarcomas, melanoma skin cancer, non-melanoma skin cancers, stomach cancer, testicular cancer, thymus cancer, thyroid cancer, uterine cancer (e.g. uterine sarcoma), transitional cell carcinoma, vaginal cancer, vulvar cancer, mesothelioma, squamous cell or epidermoid carcinoma, bronchial adenoma, choriocarinoma, head and neck cancers, teratocarcinoma, or Waldenstrom's macroglobulinemia.

In a preferred embodiment, the subject method is used to treat a solid tumor amenable to high dose radiation, for example, lung cancer, liver cancer, breast cancer, prostate cancer, ovarian cancer or pancreatic cancer; including without limitation advanced and/or metastatic cancer.

The individual is treated with high dose localized radiation, as defined above. The individual is then allowed a suitable period of time for T cell activation in situ, usually at least one week, at least two weeks, at least three weeks and not more than 6 weeks, not more than 5 weeks, not more than 4 weeks.

Collection of Activated T Cells

Following T cell activation, peripheral T cells are collected, using methods known in the art. For example leukophoresis, collection of whole blood, etc. may be used. Following collection, T cells are optionally separated from other cells by conventional methods, including flow cytometry, iso-osmolar Percoll density gradient; immunomagnetic separation technique using antibody or magnetic beads coated with antibody, etc. Where affinity selection is performed, the selection may be positive, for example separating cells that express a marker of interest, e.g. $CD4^+$, $CD8^+$, $CD3^+$, etc., or may be a negative selection, e.g. selecting against undesirable regulatory cells, e.g. $CD25^+$ cells.

In some embodiments, hematopoietic stem and/or progenitor cells such as $CD34^+$ cells are collected with the T cells for autologous reconstitution. In other embodiments hematopoietic stem and/or progenitor cells are collected from an allogeneic donor for hematopoietic reconstitution.

For collection of hematopoietic stem/progenitor cells the cells can be mobilized with granulocyte colony-stimulating factor (G-CSF). G-CSF is a potent inducer of HSCs mobilization from the bone marrow into the bloodstream, and is used to increase the number of hematopoietic stem cells in the blood of the donor before collection by leukapheresis for use in hematopoietic stem cell transplantation. It may also be given to the recipient, to compensate for conditioning regimens.

In some embodiments, $CD34^+$ hematopoietic progenitor cells are enriched. Known methods in the art can be used to enrich $CD34^+$ hematopoietic progenitor cells. For example, $CD34^+$ cells may be isolated from blood samples using immunomagnetic or immunofluorescent methods. Antibodies are used to quantify and purify hematopoietic progenitor stem cells for clinical bone marrow transplantation. In one embodiment, iso-osmolar Percoll density gradient is used to enrich $CD34^+$ cells. In another embodiment, an immunomagnetic separation technique using anti-CD34 antibody or magnetic beads coated with anti-CD34 antibody is used to enrich $CD34^+$ cells.

Chemotherapy

Following collection of T cells and optionally hematopoietic stem/progenitor cells, the individual is treated with an anti-tumor agent, or a pharmaceutically acceptable salt or prodrug thereof. The dose may be a conventional dose or a myeloablative dose. In some embodiments, the anti-tumor agents include but are not limited to antitumor alkylating agents, antitumor antimetabolites, antitumor antibiotics, plant-derived antitumor agents, antitumor organoplatinum compounds, antitumor camphothecin derivatives, antitumor tyrosine kinase inhibitors and other agents having antitumor activities, or a pharmaceutically acceptable salt thereof.

Alkylating agents are known to act through the alkylation of macromolecules such as the DNA of cancer cells, and are usually strong electrophiles. This activity can disrupt DNA synthesis and cell division. Examples of alkylating reagents suitable for use herein include nitrogen mustards and their analogues and derivatives including, cyclophosphamide, ifosfamide, chlorambucil, estramustine, mechlorethamine hydrochloride, melphalan, and uracil mustard. Other examples of alkylating agents include alkyl sulfonates (e.g. busulfan), nitrosoureas (e.g. carmustine, lomustine, and streptozocin), triazenes (e.g. dacarbazine and temozolomide), ethylenimines/methylmelamines (e.g. altretamine and thiotepa), and methylhydrazine derivatives (e.g. procarbazine). Included in the alkylating agent group are the alkylating-like platinum-containing drugs comprising carboplatin, cisplatin, and oxaliplatin.

Antimetabolic antineoplastic agents structurally resemble natural metabolites, and are involved in normal metabolic processes of cancer cells such as the synthesis of nucleic acids and proteins. They differ enough from the natural metabolites so that they interfere with the metabolic processes of cancer cells. Suitable antimetabolic antineoplastic agents to be used in the present invention can be classified according to the metabolic process they affect, and can include, but are not limited to, analogues and derivatives of folic acid, pyrimidines, purines, and cytidine. Members of the folic acid group of agents suitable for use herein include, but are not limited to, methotrexate (amethopterin), pemetrexed and their analogues and derivatives. Pyrimidine agents suitable for use herein include, but are not limited to, cytarabine, floxuridine, fluorouracil (5-fluorouracil), capecitabine, gemcitabine, and their analogues and derivatives. Purine agents suitable for use herein include, but are not limited to, mercaptopurine (6-mercaptopurine), pentostatin, thioguanine, cladribine, and their analogues and derivatives. Cytidine agents suitable for use herein include, but are not limited to, cytarabine (cytosine arabinodside), azacitidine (5-azacytidine) and their analogues and derivatives.

Natural antineoplastic agents comprise antimitotic agents, antibiotic antineoplastic agents, camptothecin analogues, and enzymes. Antimitotic agents suitable for use herein include, but are not limited to, vinca alkaloids like vinblastine, vincristine, vindesine, vinorelbine, and their analogues and derivatives. They are derived from the Madagascar periwinkle plant and are usually cell cycle-specific for the M phase, binding to tubulin in the microtubules of cancer cells. Other antimitotic agents suitable for use herein are the podophyllotoxins, which include, but are not limited to etoposide, teniposide, and their analogues and derivatives. These reagents predominantly target the G2 and late S phase of the cell cycle.

Also included among the natural antineoplastic agents are the antibiotic antineoplastic agents: Antibiotic antineoplastic agents are antimicrobial drugs that have anti-tumor properties usually through interacting with cancer cell DNA. Antibiotic antineoplastic agents suitable for use herein include, but are not limited to, belomycin, dactinomycin, doxorubicin, idarubicin, epirubicin, mitomycin, mitoxantrone, pentostatin, plicamycin, and their analogues and derivatives.

The natural antineoplastic agent classification also includes camptothecin analogues and derivatives which are suitable for use herein and include camptothecin, topotecan, and irinotecan. These agents act primarily by targeting the nuclear enzyme topoisomerase I. Another subclass under the natural antineoplastic agents is the enzyme, L-asparaginase and its variants. L-asparaginase acts by depriving some cancer cells of L-asparagine by catalyzing the hydrolysis of circulating asparagine to aspartic acid and ammonia.

Hormonal antineoplastic agents act predominantly on hormone-dependent cancer cells associated with prostate tissue, breast tissue, endometrial tissue, ovarian tissue, lymphoma, and leukemia. Such tissues may be responsive to and dependent upon such classes of agents as glucocorticoids, progestins, estrogens, and androgens. Both analogues and derivatives that are agonists or antagonists are suitable for use in the present invention to treat tumors. Examples of glucocorticoid agonists/antagonists suitable for use herein are dexamethasone, cortisol, corticosterone, prednisone, mifepristone (RU486), their analogues and derivatives. The progestin agonist/antagonist subclass of agents suitable for use herein includes, but is not limited to, hydroxyprogesterone, medroxyprogesterone, megestrol acetate, mifepristone (RU486), ZK98299, their analogues and derivatives. Examples from the estrogen agonist/antagonist subclass of agents suitable for use herein include, but are not limited to, estrogen, tamoxifen, toremifene, RU58668, SR16234, ZD164384, ZK191703, fulvestrant, their analogues and derivatives. Examples of aromatase inhibitors suitable for use herein, which inhibit estrogen production, include, but are not limited to, androstenedione, formestane, exemestane, aminoglutethimide, anastrozole, letrozole, their analogues and derivatives. Examples from the androgen agonist/antagonist subclass of agents suitable for use herein include, but are not limited to, testosterone, dihydrotestosterone, fluoxymesterone, testolactone, testosterone enanthate, testosterone propionate, gonadotropin-releasing hormone agonists/antagonists (e.g. leuprolide, goserelin, triptorelin, buserelin), diethylstilbestrol, abarelix, cyproterone, flutamide, nilutamide, bicalutamide, their analogues and derivatives.

Angiogenesis inhibitors work by inhibiting the vascularization of tumors. Angiogenesis inhibitors encompass a wide variety of agents including small molecule agents, antibody agents, and agents that target RNA function. Examples of angiogenesis inhibitors suitable for use herein include, but are not limited to, ranibizumab, bevacizumab, SU11248, PTK787, ZK222584, CEP-7055, angiozyme, dalteparin, thalidomide, suramin, CC-5013, combretastatin A4 Phosphate, LY317615, soy isoflavones, AE-941, interferon alpha, PTK787/ZK 222584, ZD6474, EMD 121974, ZD6474, BAY 543-9006, celecoxib, halofuginone hydrobromide, bevacizumab, their analogues, variants, or derivatives.

T Cell Reinfusion

T cells collected from the subject may be separated from a mixture of cells by techniques that enrich for desired cells. An appropriate solution may be used for dispersion or suspension. Such solution will generally be a balanced salt solution, e.g. normal saline, PBS, Hank's balanced salt solution, etc., conveniently supplemented with fetal calf serum or other naturally occurring factors, in conjunction with an acceptable buffer at low concentration, generally from 5-25 mM. Convenient buffers include HEPES, phosphate buffers, lactate buffers, etc.

Techniques for affinity separation may include magnetic separation, using antibody-coated magnetic beads, affinity chromatography, cytotoxic agents joined to a monoclonal antibody or used in conjunction with a monoclonal antibody, e.g. complement and cytotoxins, and "panning" with antibody attached to a solid matrix, eg. plate, or other convenient technique. Techniques providing accurate separation include fluorescence activated cell sorters, which can have varying degrees of sophistication, such as multiple color channels, low angle and obtuse light scattering detecting channels, impedance channels, etc. The cells may be selected against dead cells by employing dyes associated with dead cells (e.g. propidium iodide). Any technique may be employed which is not unduly detrimental to the viability of the selected cells. The affinity reagents may be specific receptors or ligands for the cell surface molecules indicated above. In addition to antibody reagents, peptide-MHC antigen and T cell receptor pairs may be used; peptide ligands and receptor; effector and receptor molecules, and the like.

The separated cells may be collected in any appropriate medium that maintains the viability of the cells, usually having a cushion of serum at the bottom of the collection tube. Various media are commercially available and may be used according to the nature of the cells, including dMEM, HBSS, dPBS, RPMI, Iscove's medium, etc., frequently supplemented with fetal calf serum.

The collected and optionally enriched cell population may be used immediately, or may be frozen at liquid nitrogen temperatures and stored, being thawed and capable of being reused. The cells will usually be stored in 10% DMSO, 50% FCS, 40% RPMI 1640 medium.

The T cells may be reinfused to the subject in any physiologically acceptable medium, normally intravascularly, although they may also be introduced into bone or other convenient site, where the cells may find an appropriate site for growth. Usually, at least $1 \times 10^6$ cells/kg will be administered, at least $1 \times 10^7$ cells/kg, at least $1 \times 10^8$ cells/kg, at least $1 \times 10^9$ cells/kg, at least $1 \times 10^{10}$ cells/kg, or more, usually being limited by the number of T cells that are obtained during collection.

Business Method

Also provided by the present invention is a business method of providing purified tumor cells of the present invention to a third party. As described herein, the term customer or potential customer refers to individuals or entities that may utilize methods or services of the T cell purification business. Potential customers for the T cell purification methods and services described herein include for example, patients, subjects, physicians, cytological labs, health care providers, researchers, insurance companies, government entities such as Medicaid, employers, or any other entity interested in achieving more economical or effective system for diagnosing, monitoring and treating cancer.

The following are examples of the methods and compositions of the invention. It is understood that various other embodiments may be practiced, given the general description provided above.

Example 1

Anti-Tumor T Cell Immunity Induced by High Dose Hypofractionated Radiation can be Used as Curative Therapy for Advanced Tumors The following study assessed the effect of exceptionally high single doses of radiation, which are now clinically applicable, on advanced solid tumors in mice. Our findings indicate that these high doses can cure mice with advanced colon tumors, and that efficacy is dependent on a competent immune system. The radiation not only results in a dramatic shift in the balance of tumor-infiltrating suppressive versus effector immune cells, but also induces systemic anti-tumor immunity that prevents tumor growth after challenge at distant sites, and can be transferred by T cells to adoptive hosts. Complete remissions were induced in metastatic breast tumors after primary tumor radiation, and infusion of radiation activated T cells. The findings show that single high dose radiation may have a qualitatively different effect on systemic immunity to tumors, as compared to conventional radiation with multiple small doses.

Advances in the use of confocal radiation beams targeted to tumors in 3 dimensions while minimizing radiation to adjacent normal tissues (stereotactic body radiation therapy; SBRT) allow for administration of single doses of 30 Gy or up to 3 daily doses of 20 Gy in recent clinical studies (Chang, B. K. & Timmerman, R. D. Stereotactic body radiation therapy: a comprehensive review. *Am. J. Clin. Oncol.* 30, 637-644, 2007; Brown, J. M. & Koong, A. C. High-dose single-fraction radiotherapy: exploiting a new biology? *Int. J. Radiat. Oncol. Phys.* 71, 324-325, 2008). The efficacy of SBRT to induce tumor remissions is greater than that of conventional therapy with multiple small doses of radiation. One advantage of SBRT may be induction of tumor immunity, that is not achievable with conventional radiotherapy.

Radiation can increase tumor immunogenicity by stimulating antigen presenting cells, and can promote migration and entry of T cells into tumors. In some studies, tumor radiation in mice combined with immunotherapy induced systemic immunity such that tumor growth at distant sites was slowed. However, durable complete remissions with weakly immunogenic tumors were not obtained with the combination unless the tumors were small (<1 cm) and non-metastatic.

Advanced tumors develop a microenvironment that suppresses tumor immunity by an imbalance in the makeup of tumor infiltrating mononuclear cells that favor myeloid derived suppressor cells (MDSCs) and tumor associated macrophages (TAMs) over conventional $CD8^+$ T cells, and $CD4^+CD25^+FoxP3^+$ Treg cells over $CD8^+$ T cells. In addition, expression of negative co-stimulatory molecules such as PD-1 and Tim-3 on $CD8^+$ T cells results in an "exhausted" phenotype with associated immune dysfunction. Clinical studies have shown that high levels of immunosuppressive MDSCs and Treg cells or increased expression of negative co-stimulatory receptors on T cells within tumor biopsies were correlated with a poor prognosis, whereas high levels of conventional $CD8^+$ T cell were correlated with a good prognosis.

The study described herein determined whether high doses of radiation, similar to those used in SBRT, administered to poorly immunogenic advanced CT26 colon and 4T1 breast tumors in mice can induce curative systemic immune responses that will prevent tumor growth after challenge at distant sites, and whether anti-tumor immunity can be transferred by radiation activated T cells. In addition, the impact of radiation on the tumor infiltrating mononuclear cells was studied to determine whether the immune suppressive microenvironment can be reversed by the high dose radiation therapy.

Results

Treatment of CT26 tumors with radiotherapy induces complete remissions, and systemic immunity that can be transferred with T cells: FIG. 1A shows the growth of CT26 tumor cells injected subcutaneously ($2.5 \times 10^4$ cells) into the hind quarter of wild type BALB/c mice. There was a progressive increase in tumor volume, and none of the tumors developed spontaneous regressions. By day 21 the tumors were advanced, and nodules were at least 1 cm in diameter. When tumors were given a single dose of 15 Gy local tumor irradiation (LTI) at day 21 using lead jigs developed for targeting only the 1.0-1.5 cm diameter tumor nodule, transient slowing of tumor growth was observed in 7 of 8 mice. A complete, sustained remission in tumor growth was achieved in 1 of 8 mice. When the dose was increased to 20 Gy then 3 of 5 mice developed complete tumor remissions, and when the dose was increased to 30 Gy, 13 of 15 mice achieved complete remissions, and mice survived for at least 100 days (FIG. 1A). Further observations showed no recurrence of tumors up to 180 days. Although a single dose of 30 Gy was highly effective in treating the tumors, 10 daily doses of 3 Gy each induced remissions in only 1 of 8 tumors, and survival of tumor bearing mice was similar to that with a single dose of 15 Gy (FIG. 1A; $p > 0.05$).

The cured wild type mice observed for 100-150 days were challenged with another subcutaneous injection ($5.0 \times 10^5$ CT26 tumor cells), and 9 of 12 tumors resolved after a brief increase in volume. Three out of 12 tumors grew progressively (FIG. 1B), and mice with the latter tumors died within 100 days (FIG. 1B). In a previous study (Filatenkov et al. *J. Immunol.* 1; 183(11):7196-203, 2009), we showed that a single subcutaneous vaccination with $1 \times 10^6$ CT26 tumor cells that were irradiated in vitro with 50 Gy and mixed with the adjuvant, CpG, was able to protect about 50% of BALB/c mice from subsequent challenge with $2.5 \times 10^4$ tumor cells. However, when the vaccinated mice were challenged with $5.0 \times 10^5$ tumor cells, most tumors grew progressively, and about 90% of challenged hosts died (FIG. 1B). Thus, the protection afforded by the single dose of LTI was more potent than the vaccination procedure for this weakly immunogenic tumor ($p = 0.01$).

In order to determine whether T cells from mice with complete remissions of tumors for at least 100 days after LTI treatment can adoptively transfer the ability to effectively treat CT26 tumors, we used the scheme outlined in the diagram in FIG. 1C. T cells were purified from the spleens of the cured mice using anti-Thy1.2 columns, and combined with T cell depleted bone marrow cells from the donors. The marrow and T cells were injected i.v. into irradiated adoptive recipients that had been given a subcutaneous injection of CT26 tumor cells, and then a single dose of 8 Gy TBI 7 days later. The tumor bearing recipients all developed complete remissions and survived for at least 100 days (FIG. 1C). When the experiment was repeated using T cells from the spleen of untreated normal mice combined with T cell depleted marrow cells, the adoptive transfer did not induce remissions in tumor growth, and all recipients died by day 40 (FIG. 1C). The survival of the latter recipients was similar to that of recipients given tumors without subsequent radiation and transplantation.

Figure 2B:
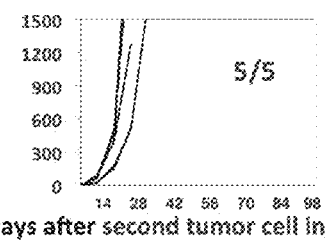
Figure 2B:
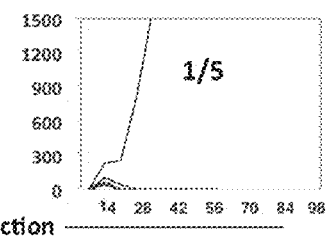
Figure 2C:
Figure 2C:
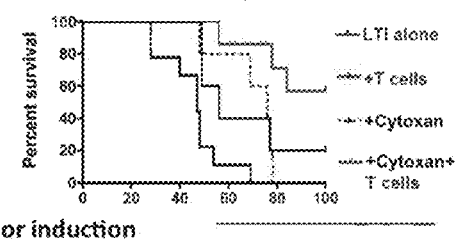

FIG. 2A shows that mice with 21 day tumors had no protection against tumor challenge on the contralateral flank at day 21, and all second tumors grew progressively. Similarly, when mice with 21 days tumors were given 30 Gy LTI at day 21 with a contralateral tumor challenge on the same day, all second tumors grew progressively (FIG. 2B). In contrast, if challenge was delayed until 30 days after LTI, then only 1 of 5 second tumors grew progressively. This indicated that tumor immunity does not develop immediately after LTI, but becomes manifest after a few weeks. In further studies, the impact of T cell depletion or immune cell deficiency on the ability of LTI to induce complete tumor remissions was determined. FIG. 2C shows that about 90% of mice with 21 day tumors survived more than 100 days after LTI. However, none of the mice depleted of $CD8^+$ T cells by the injection of anti-CD8 mAb, survived for more than 100 days ($p<0.0001$). About 40% of mice depleted of $CD4^+$ T cells survived for at least 100 days ($p<0.01$) as compared to mice without mAb. Depletion of both $CD4^+$ and $CD8^+$ T cells with anti-thymocyte serum (ATS) reduced the survival of all mice to less than 62 days. The survival of mice in that latter group was significantly shorter than with either depletion of $CD4^+$ or $CD8^+$ T cells alone ($p<0.01$).

Figure 2E:
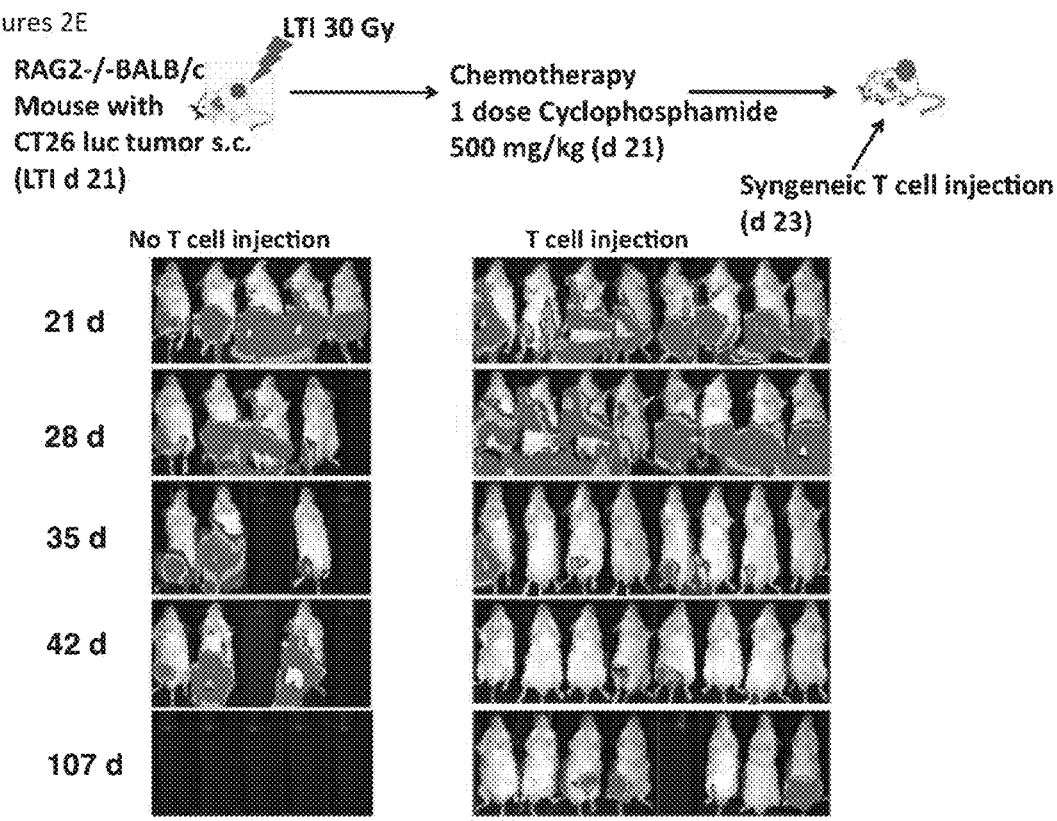

In some experiments the CT26 cells were injected subcutaneously into immunodeficient RAG-$2^{-/-}$ mice, and then treated with 30 Gy LTI at day 21. FIG. 2D shows that the tumors in these mice grew progressively, and none of the tumor bearing mice survived beyond 70 days. We injected T cells from the spleen of normal wild type BALB/c mice i.v. into the tumor bearing RAG-$2^{-/-}$ mice immediately after LTI. The injection of T cells improved survival significantly ($p<0.05$), but only 20% of mice survived for more than 100 days (FIG. 2D). We injected mice with a single dose of cyclophosphamide (CY) just after the LTI, and injected the wild type T cells thereafter. The combination of LTI, CY and T cells significantly improved survival of the mice as compared to LTI alone ($p<0.001$) such that 60% of mice survived at least 100 days (FIG. 2D). None of the mice given LTI and CY without T cells survived beyond 80 days, and the addition of T cells significantly improved survival ($p<0.001$). The effect of T cell injections on CT26 tumor growth in RAG2$-/-$mice given LTI and CY was assessed by bioluminescence imaging (BLI) of luciferase gene transduced CT26 tumor cells. FIG. 2E shows the experimental scheme and the BLI results at weekly intervals from day 21, the time of LTI. CY was injected on day 23 with or without a T cell injection on day 25. There was considerable spread of tumors by day 21 in groups with and without T cell injections. By day 28 most mice had tumor extending above the diaphragm associated with development of tumor nodules in the lungs. By day 35, there were marked differences in the RAG2$-/-$ mice groups with or without T cells; 2 of 5 mice in the latter group died, when all in the T cell injected group survived and showed marked reduction of tumor signals. Tumor clearing continued in the T cell injection group, and by day 42, 6 out of 8 mice showed no tumor signal. In contrast, the group without the T cell injection showed continued tumor growth, and all of the mice died by day 107.

Figure 3A:
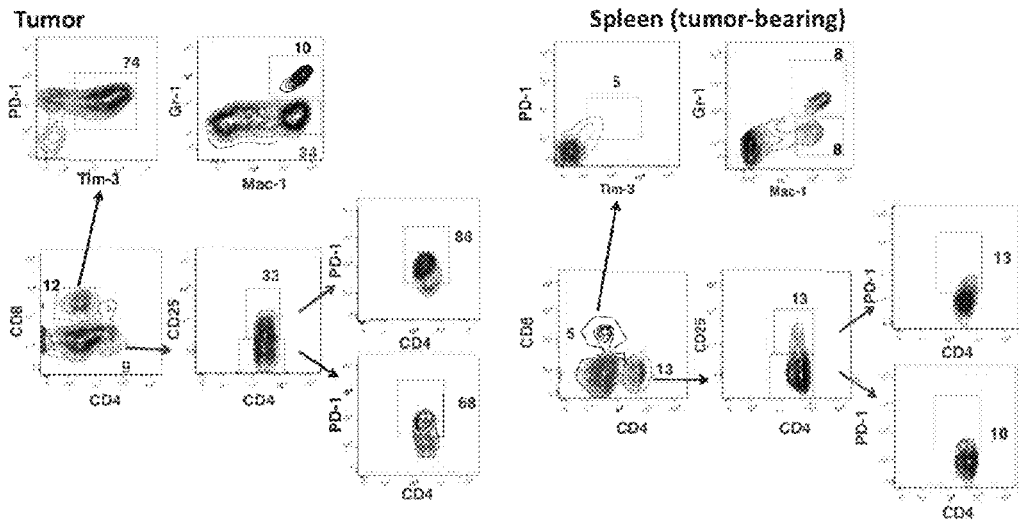
FIGS. 3A-3C. Comparison of infiltrating mononuclear cells in tumors, and in spleens of mice with or without tumors.

Analysis of CT26 Tumor Infiltrating Mononuclear Cells:

The untreated 21 day CT26 tumors in wild type mice were examined for the composition of the infiltrating mononuclear cells. The subcutaneous tumors were excised and single cell suspensions were stained for T cell markers as well as the CD11b and Gr-1 markers of myeloid derived suppressor cells (MDSCs) and tumor associated macrophages (TAMs). The $CD8^+$ and $CD4^+$ T cells accounted for about 12 and 9% respectively of the mononuclear cells in the representative two color FACS patterns (FIG. 3A). Among the gated $CD8^+$ cells, about 74% expressed the PD-$1^+$Tim-$3^+$ phenotype that has been described for "exhausted" cells in mice with tumors or with chronic viral infections (Sakuishi et al. *J. Exp. Med.* 207, 2187-2194, 2010). Among the $CD4^+$ cells, about 33% were $CD25^+$, and among the latter, about 60% were FoxP3$^+$ Treg cells. In addition, the majority of the $CD4^+CD25^+$ and $CD4^+CD25^-$ T cells expressed the negative co-stimulatory receptor, PD-1, that has been reported previously to be upregulated on tumor infiltrating T cells. Interestingly, the tumor mononuclear cells contained about 10% CD11b$^+$Gr-$1^+$ cells with the MDSC phenotype, and 34% that were CD11b$^+$Gr-$1^-$ TAMs. The MDSCs and TAMS expressed high levels of PDL-1 (FIG. 5).

Figure 3B:
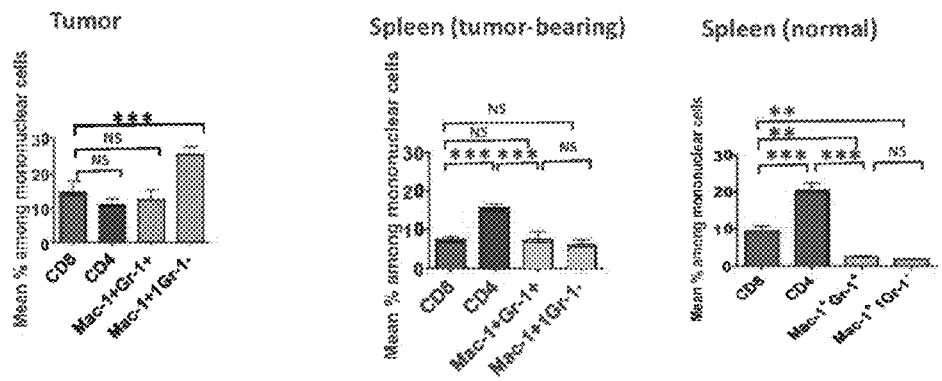

At the same time that the tumor infiltrating cells were examined, the spleens from these mice were examined also (FIGS. 3 A and B). The $CD8^+$ and $CD4^+$ T cells accounted for about 5 and 13% of mononuclear cells respectively, and about 13% of $CD4^+$ cells were $CD25^+$, and only 5% of $CD8^+$ cells were PD-$1^+$Tim-$3^+$. The mean percentage of $CD25^+$ cells among $CD4^+$ cells in the normal spleen was about 11%, and the mean percentage of PD-$1^+$Tim-$3^+$ cells among $CD8^+$ cells was about 1% (FIG. 3B). Whereas, the majority of $CD4^+$ cells in the tumor were PD-$1^+$, only about 10-13% in the spleen were PD-$1^+$ in the flow patterns shown in FIG. 3A. The CD11b$^+$Gr-$1^+$ and CD11b$^+$Gr-$1^-$ cells in the spleen each accounted for about 8% of mononuclear cells. FIG. 3B compares the mean percentages of the $CD8^+$, $CD4^+$ T cells, MDSCs, and TAMs in the tumors, and spleens from the tumor-bearing and normal mice. The mean percentages of the T cells and MDSCs were not significantly different in the tumors, and the mean percentage of TAMs was increased about 2 fold as compared to that of the $CD4^+$ or $CD8^+$ T cells and MDSC. In contrast, the percentages of $CD4^+$ and $CD8^+$ T cells were considerably higher than MDSCs or TAMs in the normal spleen. The mean percentages of MDSCs in the tumors was increased as compared to the spleen of the tumor bearing mice ($p<0.01$), and mean percentages of MDSCs in both tissues were increased as compared to normal spleens ($p<0.001$).

Figure 3C:
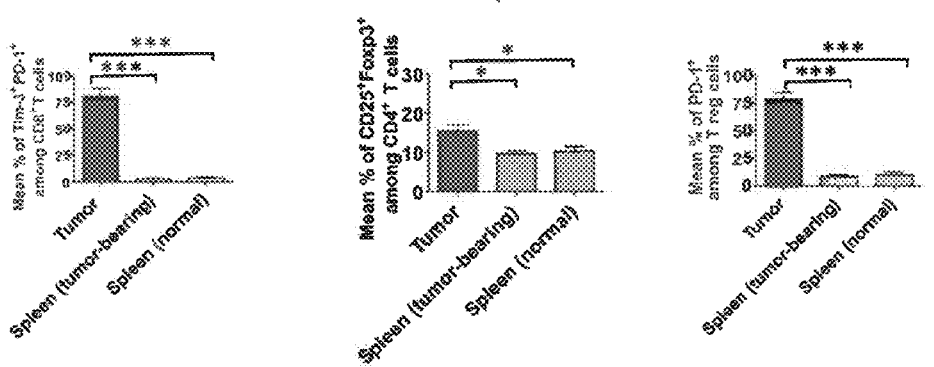
Figure 6:
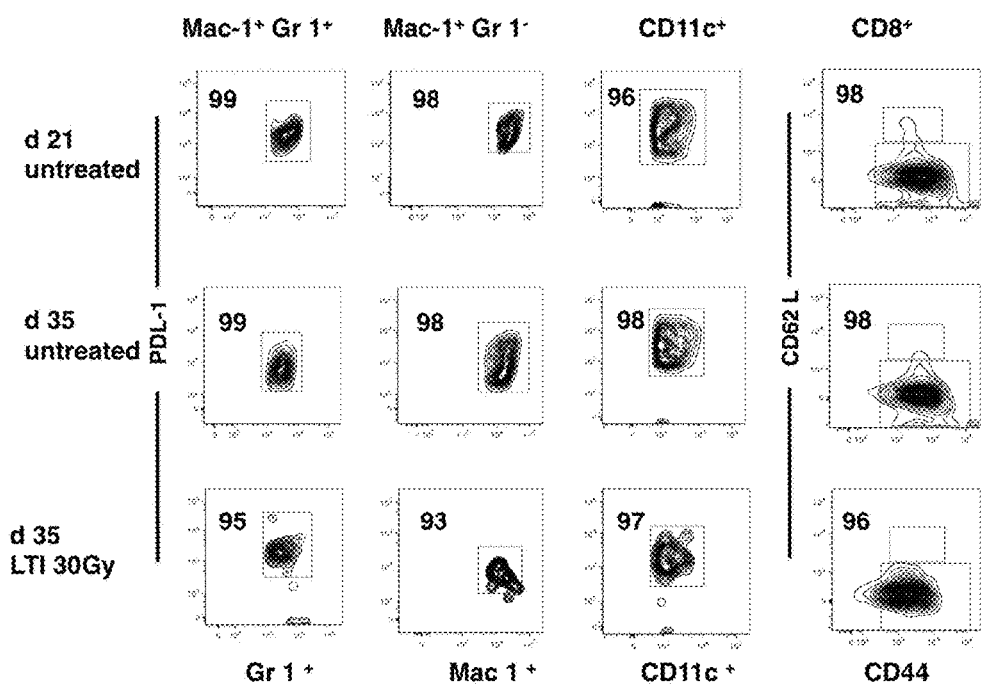
FIG. 6. PDL-1 and CD62L expression of tumor-infiltrating cells. Tumor-infiltrating cells were analyzed at day 21 after CT26 tumor implantation, as well as at day 35 in untreated animals or animals that received LTI 30 Gy at day 21. PDL-1 expression was analyzed on MDSCs (Mac-1$^+$ Gr1$^+$), TAMs (Mac-1$^+$ Gr1$^-$) suppressor cells, as well as DCs (CD11c$^+$). CD44 and CD62L expression was analyzed on CD8+ tumor infiltrating cells. Representative stainings are shown.

FIG. 3C compares the mean percentages of PD-$1^+$Tim-$3^+$ cells among $CD8^+$ T cells in the tumors and spleens. Whereas the percentage in the tumors was about 80%, that in the spleen of tumor bearing or non-tumor bearing mice was less than 5%. Similarly, the mean percentage of PD-$1^+$ cells among $CD4^+CD25^+$FoxP3$^+$ Treg cells was about 80% in tumors, and was less than 10% in spleens. The mean percent of Tregs among $CD4^+$ T cells was significantly increased in the tumors as compared to the spleens.

Radiotherapy Changes Composition of Tumor Infiltrating Cells:

Day 21 tumors were irradiated with a single dose of 30 Gy and the infiltrating cells were examined at day 35. Controls received no radiation or 10 doses of 30 Gy each. FIG. 4A shows the composition of infiltrating cells at day 35 in mice without radiation. The balance of T cells, MDSCs and TAMs was similar to that observed in day 21 tumors before radiation (FIG. 3). However, tumors given radiation showed a significant increase in the percentage of $CD8^+$ T cells from a mean of about 15% without radiation to about 65% ($p<0.01$) with radiation as shown in representative flow cytometry patterns and bar graphs in FIGS. 4A and 4B. The $CD8^+$ T cells were all almost all of the effector memory (CD62L$^-$CD44$^+$) phenotype (FIG. 5), and still showed the "exhausted" phenotype. Interestingly, the combined percentages of MDSCs and TAMs were significantly reduced from about 46% to about 7% (p<0.001) after radiation (FIGS. 4 A and B). The percentage of Tregs was also significantly reduced (p<0.001), and the high level of PD-1 expression persisted on the CD4$^+$ Tcon and Treg cells (p>0.05) (FIG. 4 D). The changes in the percentages of cell types resulted in marked increases in the ratio of CD8$^+$ T cells to MDSCs, to TAMs, and to Tregs (p<0.0001) (FIG. 4E). Although the single dose of 30 Gy induced a profound change in the composition of cells, the composition after 10 doses of 3 Gy was similar to tumors without radiation (FIG. 4).

Use of T Cell Therapy in Preventing Progression of 4T1 Breast Tumor Metastases after Radiotherapy:

In additional experiments, we studied the effect of high dose radiation on another tumor, the 4T1 breast tumor in BALB/c mice that metastasizes to the lungs after subcutaneous injection. FIG. 5A shows the growth of the 4T1 tumor transduced with the luciferase gene using BLI after subcutaneous injection into the hind quarter. All mice died of tumor progression within 55 days whether or not tumor cells were transduced with the luciferase gene (FIG. 5 A), and growth was similar to that reported for orthotopic injections. Both BLI and histopathological analysis at day 21 showed that tumors had spread to the lungs by that time. (FIGS. 5 B and C). When 30 Gy was administered to 14 day tumors slowing of the growth was observed without development of complete remissions. However 3 daily doses of 20 Gy each resulted in complete remissions in 2 out of 5 mice (FIGS. 5 A and B) that survived for more than 100 days. Thus, 4T1 tumors required higher total doses to achieve complete remissions as compared to CT26 tumors. In further studies, tumors were allowed to grow for 21 days before treatment as in the experiments with CT26 tumors. A single dose of 30 Gy LTI showed only modest slowing of local tumor growth, and had little impact on metastatic spread of tumor and survival. When the tumors were irradiated with 3 daily doses of 20 Gy each, the subcutaneous tumor markedly regressed, but spread to distant sites as judged by BLI. Seven of eight mice died by day 84, with 1 of 8 in remission (FIG. 5D). When a single dose of CY was given after the third dose of LTI, the progression of tumor growth was slowed, but 6 of 8 mice died by day 84 and 1 relapsed at day 98 (FIG. 5E).

Based on the use of CY followed by T cell infusion in the RAG-2$^{-/-}$ experiments described above, a group of mice were treated with LTI followed by splenectomy within 24 hours (FIG. 5 F). The splenic T cells were enriched using an anti-Thy1.2 mAb column, and cryopreserved. Just after splenectomy, the mice were given a single dose of CY, and 2.5×10$^6$ T cells were infused i.v. 48 hours later. In this group, 4 of 7 showed no evidence of tumor at days 84 and 98. Survival of the group given LTI+CY+ T cells was significantly increased (p<0.01) as compared to the group given LTI+CY without T cells. (FIG. 5 F). Thus, the combination of LTI, CY, and T cell therapy was more effective than either LTI alone or in combination with CY.

These data show that high dose hypo-fractionated tumor radiation similar to SBRT currently used in humans (see Chang & Timmerman Am. J. Clin. Oncol. 30, 637-644, 2007; Brown & Koong Int. J. Radiat. Oncol. Biol. Phys. 71, 324-325, 2008) can induce complete remissions and potent systemic immunity that is transferable with T cells. A second goal was to determine whether T cell therapy can enhance the efficacy of radiotherapy in the treatment of metastatic tumors. In order to optimize the therapeutic efficacy of local radiation of large (>1 cm diameter) subcutaneous CT26 colon tumors growing in BALB/c mice, single doses of radiation targeted to the tumor were escalated from 15 to 30 cGy. At the highest dose, about 85% of tumor bearing mice developed durable complete remissions for up to 6 months. Almost all mice with complete remissions for at least 100 days were protected against a second challenge with CT26 tumor cells on the contralateral flank. Protection after radiation did not occur immediately, since tumor challenge at a distant site on the same day as the radiation resulted in progressive growth of all second tumors despite the resolution of the primary tumors unless tumor challenge was delayed for 30 days after radiation. The results indicate that resolution of the primary tumors is best explained by a combination of direct cytotoxic effects of radiation on tumor cells and stroma in the radiation field in combination with the development of systemic immunity thereafter.

Splenic T cells obtained from mice in complete remission for more than 100 days after tumor radiation were able to transfer the anti-tumor immunity to adoptive hosts that were bearing CT26 tumors. Tumor radiation in T cell depleted wild-type or immunodeficient RAG-2$^{-/-}$ mice failed to induce complete remissions. Surprisingly, intravenous injection of T cells from normal wild type mice did not restore the efficacy of radiation in RAG-2$^{-/-}$ mice, but the administration of a single dose of CY after radiation and just before the injection of T cells resulted in a marked improvement in remissions and survival. Administration of CY kills tumor cells, increases the function of antigen presenting cells by altering the make up of dendritic cell subsets, and selectively depletes Treg cells. The combination of LTI, CY, and T cell therapy was effective in preventing widespread dissemination of tumors in the RAG2$^{-/-}$ mice.

The composition of mononuclear cells that infiltrate the CT26 tumors was studied before and after radiation in order to elucidate the mechanisms of immune changes. As in previous studies, there were three important changes before radiation in the intratumoral mononuclear cells as compared to those in the normal spleen; 1) there was an imbalance in the percentage of monocytic (TAMs) and myeloid (MDSCs) suppressor cells versus CD8$^+$ T cells favoring the suppressor cells, 2) there was an imbalance favoring the CD4$^+$CD25$^+$ FoxP3$^+$ Treg cells as compared to CD8$^+$ T cells, and 3) the CD8$^+$ T cells expressed the PD-1$^+$Tim-3$^+$ "exhausted" phenotype and the Tregs expressed the activated PD-1$^+$ phenotype. A single dose of 30 Gy reduced the ratio of TAMs and MDSCs versus CD8$^+$ T cells, and the ratio of Treg versus CD8$^+$ T cells. A balance favoring CD8$^+$ T cells over suppressor cells correlates with a favorable prognosis in studies of human tumors.

In additional experiments designed to extend the approach to breast tumors, subcutaneous injection of 4T1 tumor cells resulted in local growth followed by the development of metastases in the lungs. The 4T1 tumors required 3 daily doses of 20 Gy each to reverse primary tumor growth, but failed to control metastases. Based on the RAG2$^{-/-}$ results with CT26 tumors, immediately after 4T1 tumor radiation mice were splenectomized and the splenic T cells were harvested and cryopreserved. A single dose of CY was administered thereafter, and the cryopreserved T cells were infused 2 days after the chemotherapy. This combination induced durable complete remissions. Although radiotherapy combined with immunotherapy with anti-CTLA4 antibodies in previous studies resulted in a significant increase in survival of 4T1 tumor bearing mice as compared to either modality alone, there were no durable complete remissions.

In conclusion, the studies show that high dose hypofractionated tumor radiation is able to induce systemic immunity to tumors that is transferable with T cells. The T cell therapy approach effectively treated metastatic disease when used in combination with both radiation and chemotherapy. Since all three completions can be applied clinically, a similar combination can be effective in patients with advanced solid tumors.

Materials and Methods

Animals. Wild-type male BALB/c (H-2$^d$) mice, and male BALB/c RAG2$^{-/-}$ mice, were purchased from Jackson Laboratories (Bar Harbor, Me.). Mice were 5-8 weeks old. The Stanford University Committee on Animal Welfare (Administration Panel of Laboratory Animal Care) approved all mouse protocols used in this study.

Cell lines. The CT26 cell line (an N-nitro-N-methylurethane-induced BALB/c murine colon carcinoma) was purchased from ATCC (Manassas, Va.). The 4T1 cell line (spontaneously arising) was also obtained from ATCC. The 4T1-LUC/GFP and CT26-LUC/GFP cell lines were lentiviraly transduced. The lentiviral vector pHR-IG was made by Dr. Yoshitaka Akagi. The GFP-firefly luciferase fusion (GLF) gene was subcloned from pJW.GFP-yLuc (kindly provided by Dr. M. H. Bachmann) into pHR2 to generate pHR2-GLF. Lentiviral particles expressing GLF were prepared as described before. Briefly, 293T cells were plated in 175 cm$^2$ flasks, and the next day, near-confluent cells were co-transfected with 45 µg lentiviral vector together with packaging and VSV-G-expressing vectors (3:2:1 ratio) in presence of 25 µM chloroquine (Sigma). WT 4T1 and CT26 cells were seeded in a 6 well plate at 0.25×106 cells/well and incubated overnight in a 37° C. incubator. Titrated virus was then used to transduce the cell lines in the presence of protamine sulfate (10 µg/ml) to enhance transduction efficiency. Stable lentiviral transductants were then sorted 4 times for GFP fluorescence (100% purity) using a FACS DIVA cell sorter. Sorted cells were expanded and screened for bioluminescence using an Xenogen IVIS spectrum (Caliper Life Sciences; Hopkinton, Mass.), as well as GFP. Cell lines were maintained in RPMI-1640 complete medium supplemented with 10% fetal calf serum, L-glutamine, 2 mercaptoethanol, streptomycin and penicillin.

Vaccination. Tumor vaccination was performed as previously described 33. Five-week-old male BALB/c mice were immunized by subcutaneous injection of 1×106 irradiated (50 Gy) CT26 cells and 30 µg of CpG. Oligonucleotide containing unmethylated CG motifs (CpG) (TCCATGACGTTCCTGACGTT (SEQ ID NO:1)) was synthesized and phosphorothioate-stabilized by Invivogen (San Diego, Calif.).

Irradiation. Total body irradiation was performed with a Philips X-ray unit (200 kV, 10 mA; Philips Electronic Instruments Inc., Rahway, N.J.) at a rate of 84 cGy/min with a 0.5 mm Cu filter. For local tumor irradiation, unanesthetized mice were placed in lead jigs through which established tumors in the hind quarter were protruded for irradiation to an area of approximately 2 cm diameter. Irradiation was performed with a Phillips X-ray unit operated at 200 kV with the dose rate of 1.21 Gy/min (20 mÅ with added filtration of 0.5 mm copper, the distance from X-ray source to the target of 31 cm, and a half value layer of 1.3 mm copper).

Cell preparation, splenectomy, and collection of T cells for autologous transplantation. Single cell suspensions of bone marrow and spleen were prepared according to previously described procedures. Some samples were enriched either for Thy1.2$^+$ cells with anti-Thy1.2-biotin monoclonal antibodies (mAb) (5a-8; Caltag, Burlingame, Calif.) and streptavidin-magnetic beads (Miltenyi Biotech) respectively using the MidiMACS system (Miltenyi Biotech, Auburn, Calif.). Enriched cells were stained with anti-TCR-allophycocyanin (APC) and anti-CD4 or anti-CD8-fluorescein isothiocyanate (FITC) mAbs to check for purity, and preparations were uniformly at least 95% pure.

FACS Aria (Becton Dickinson, Mountain View, Calif.) was used for analysis with FlowJo software (TreeStar, Ashland, Oreg.). After sorting cells were checked by FACS reanalysis and determined to be >99% pure. Collected T cells were cryopreserved with 10% DMSO and frozen in liquid nitrogen. Splenectomy was performed under isoflurane anesthesia. After laparotomy, splenic vessels were ligated, and the spleen was removed. Abdominal wall was closed with single stitches (silk 5-0). Intraperitoneal injection of 500 mg/kg of cyclophosphamide (Sigma Aldrich) was performed within 76 hours after splenectomy.

In vivo BLI imaging. In vivo BLI was performed according to the method of Edinger et al. Briefly, mice were injected intraperitoneally with luciferin (10 µg/g body weight). Ten minutes later, mice were imaged using an IVIS100 charge-coupled device imaging system (Xenogen) for 5 minutes. Imaging data were analyzed and quantified with Living Image software (Xenogen).

In vivo depletion of T cells. Anti-CD4, anti CD8 monoclonal antibodies were obtained from Dr. S. Schoenberger, La Jolla Institute for Allergy and Immunology (La Jolla, Calif.). Depletion of CD4 cells in vivo was performed by intraperitoneal administration of 150 mg GK1.5 antibody on days 1,3,5 after irradiation. Mice were depleted of CD8 T cells by i.p. injection of 100 mg of the monoclonal anti-CD8 antibody, 2.43, on days 1,3,5 after irradiation.

Rabbit antithymocyte serum (ATS) was purchased from Accurate Chemical and Scientific (Westbury, N.Y.). BALB/c recipients were injected intraperitoneally with 0.05 mL of ATS in 0.5 mL saline on days 0, 2 and 4 after irradiation.

Histopathology. Animals were euthanized when moribund as per Stanford Animal Welfare protocol guidelines, or at 100 days after transplantation if they survived without morbidity. Histopathological specimens were obtained from lungs and livers of hosts. Tissues were fixed in 10% formalin, stained with hematoxylin and eosin and images were obtained using an Eclipse E1000M microscope (Nikon, Melville, N.Y., USA) as described before.

Analysis of tumor and spleen mononuclear cells by staining and flow cytometry. Single-cell suspensions were prepared from spleens and tumor nodules of BALB/c recipients. The following mAbs were used for flow cytometric analysis: unconjugated anti-CD16/32 (2.4G2 BD Biosciences), anti-CD4-FITC (RM4-5 BD Biosciences), anti-TCR-APC (H57-597 BD Biosciences), anti-CD8-APC-Cy7, (53-6.7 BD Biosciences), anti-PD-1 FITC (29F.1A12, Biolegend), anti-Tim-3 PE (B8.2C12 Biolegend), anti-FoxP 3 APC (FJK-16s, eBioscience), anti-Gr-1 PE (RB6-8C5, Biolegend), anti-CD11b FITC (M1/70, Biolegend), anti-CD62L (MEL-14, Biolegend), anti CD44 PerCP-Cy5 (IM-7, eBioscience), anti-Thy1.1PE-Cy7 (HIS51, eBioscience), anti-Thy1.2-biotin (5a-8; Caltag). Streptavidin-PE was from Beckton Dickenson. All stainings were performed in PBS/ 1% calf serum in the presence of purified anti-CD16/32 mAbs.

Statistical analysis. Kaplan-Meier survival curves were generated using Prism software (SAS Institute Inc., Cary, N.C.), and statistical differences were analyzed using the log-rank (Mantel-Cox) test. Statistical significance in differences between mean percentages of cells in spleens and tumors was analyzed using the two-tailed Student's t-test of means.

What is claimed is:

1. A method for treating a cancer in a subject, the method comprising:
   a. activating T cells with a high dose of localized radiation at a tumor site;
   b. collecting a population of cells comprising the activated T cells; and
   c. administering the collected population of cells to the subject, thereby treating the cancer.

2. The method of claim 1, wherein the high dose of localized radiation comprises a total dose of 20 to 40 Gy.

3. The method of claim 2, wherein the high dose of localized radiation is delivered in a single dose.

4. The method of claim 2, wherein the high dose of localized radiation is delivered in fractionated doses over a period of time of not more than one week.

5. The method of claim 1, wherein (a) is performed over a time period from 2 to 6 weeks.

6. The method of claim 1, further comprising purifying the activated T cells from regulatory T cells and purge tumor cells in the collected population of cells.

7. The method of claim 1, wherein the collected population of cells comprises allogeneic cells.

8. The method of claim 1, wherein the collected population of cells comprises autologous cells.

9. The method of claim 1, wherein the collected population of cells comprises CD34+ cells.

10. The method of claim 1, wherein activated T cells comprises CD8+ T cells, wherein the CD8+ T cells are activated by the high dose of localized radiation at the tumor site to recognize the cancer.

11. The method of claim 1, wherein the collected population of cells comprises at least 1×106 CD8+ T cells.

12. The method of claim 11, further comprising enriching the CD8+ T cells from the collected population of cells.

13. The method of claim 11, further comprising purifying the CD8+ T cells from the collected population of cells.

14. The method of claim 1, wherein administering the collected population of cells provides for durable remission of the cancer.

15. The method of claim 1, wherein administering the collected population of cells prevents growth of metastases at a site other than the tumor.

16. The method of claim 1, wherein administering the collected population of cells stimulates an immune system of the subject to target cancer cells.

17. The method of claim 1, wherein the cancer is in an advanced state.

18. The method of claim 1, wherein the cancer is metastatic.

19. The method of claim 1, wherein the subject has been treated with an effective dose of chemotherapy prior to administering the collected population of cells.

20. The method of claim 19, wherein the effective dose of chemotherapy is a non-myeloablative dose.

21. The method of claim 19, wherein the effective dose of chemotherapy is a myeloablative dose.

22. The method of claim 1, wherein the cancer is a liver cancer, a lung cancer, a brain cancer, a pancreas cancer, a melanoma cancer, or a breast cancer.

23. The method of claim 1, wherein the subject is a mammal.

* * * * *